United States Patent [19]

Fischer

[11] Patent Number: 5,454,881
[45] Date of Patent: Oct. 3, 1995

[54] METHOD FOR MARKING THIN WALLED TUBES

[75] Inventor: Mark F. Fischer, Colorado Springs, Colo.

[73] Assignee: Colorado Laser Marking, Inc., Colorado Springs, Colo.

[21] Appl. No.: 210,663

[22] Filed: Mar. 18, 1994

Related U.S. Application Data

[63] Continuation of Ser. No. 801,788, Dec. 4, 1991, abandoned.

[51] Int. Cl.$^6$ .............................. B05D 3/06; B23K 26/08; B23K 26/18; A61M 5/00
[52] U.S. Cl. .......................... 148/241; 427/2.3; 427/696; 219/121.8; 219/121.84; 604/264
[58] Field of Search .................... 604/164, 264, 604/280; 219/121.6, 121.61, 121.78, 121.8, 121.84; 427/2, 553, 556, 596, 2.3, 554, 584, 596; 156/643; 148/241

[56] References Cited

U.S. PATENT DOCUMENTS

| | | | |
|---|---|---|---|
| 4,560,580 | 12/1985 | Needham et al. | 427/53.1 |
| 4,690,138 | 9/1987 | Herden | 128/207.15 |
| 4,720,618 | 1/1988 | Stamer et al. | 219/121 LA |
| 4,861,620 | 8/1989 | Azuma et al. | 427/53.1 |
| 4,922,077 | 5/1990 | Gordon | 219/121.68 |
| 5,045,071 | 9/1991 | McCormick et al. | 604/280 |
| 5,084,022 | 1/1992 | Claude | 604/164 |

OTHER PUBLICATIONS

George, Joy Preparation of Thin Films Mercel Dekker Inc. 1992 pp. 278–279.

*Primary Examiner*—Shrive Beck
*Assistant Examiner*—Bret Chen
*Attorney, Agent, or Firm*—Beaton & Folsom

[57] ABSTRACT

A method for marking thin walled tubes, using a laser. To prevent warping and to maintain the structural integrity of the tube, coolant is injected into the tube while it is being marked. To further prevent warping and to maintain the structural integrity of the tube, each mark is composed of a set of relatively thin marks, each separated by an unmarked space, and the tube and the laser are moved relative to one another so that the series of marks can be generated.

10 Claims, 4 Drawing Sheets

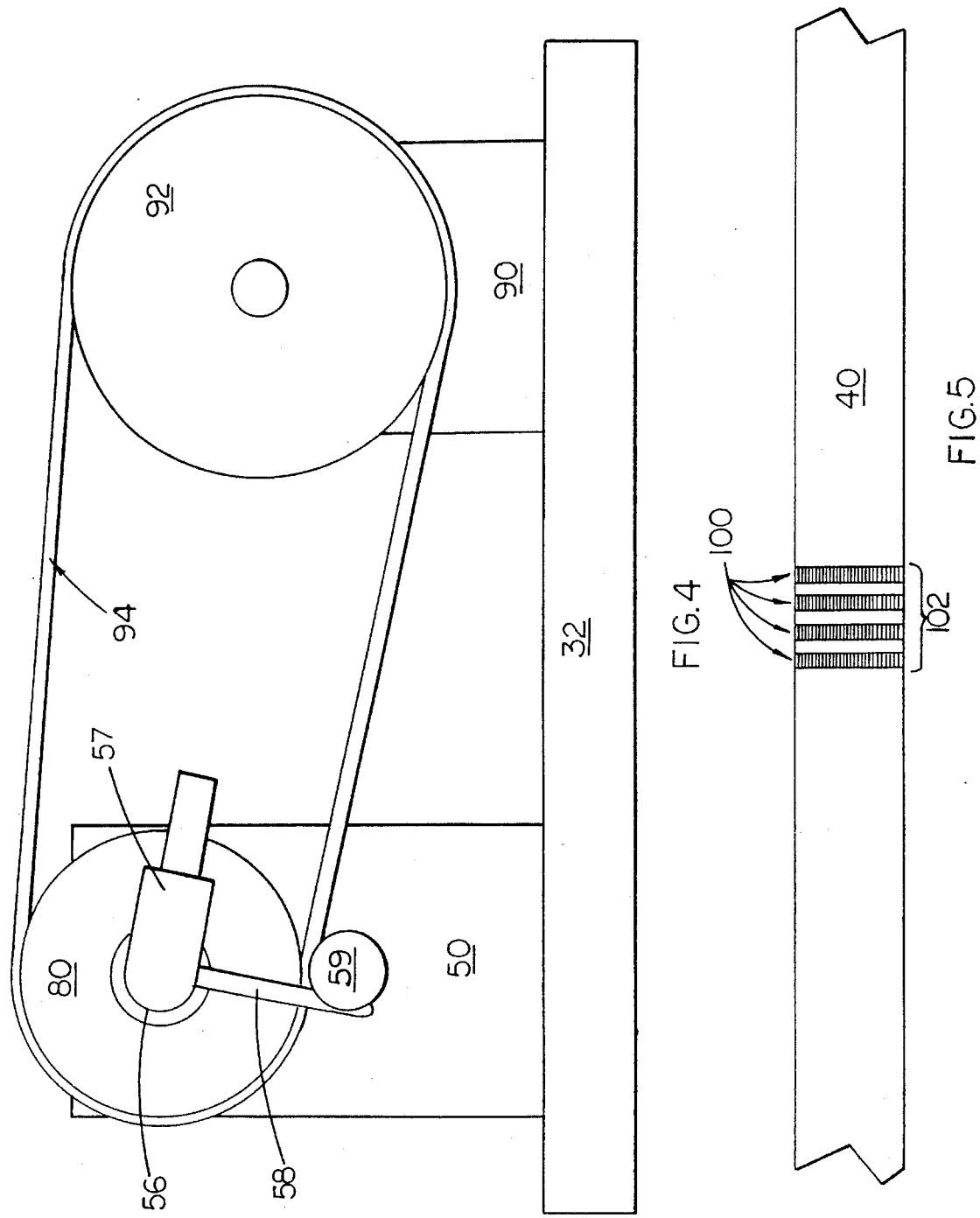

METHOD FOR MARKING THIN WALLED TUBES

This is a continuation of application(s) Ser. No. 07/801,788 filed on Dec. 4, 1991, now abandoned.

FIELD OF THE INVENTION

This invention relates to marking thin walled tubes, and more particularly to using a laser system to do so while preventing warping of the tube and preserving its structural integrity. The invention has particular utility for marking stainless steel cannula in such a way as to provide high contrast reference markings along the circumference of the cannula without distortion of the cannula. The reference markings give medical personnel the ability to accurately measure the penetration of the cannula in procedures such as amniocentesis and biopsy.

BACKGROUND OF THE INVENTION

Medical procedures such as amniocentesis and biopsy typically involve the insertion of a stainless steel cannula into a living body and the insertion and manipulation of certain other instruments through the lumen of the cannula.

Although the depth of penetration of the cannula into the body can be gauged by monitoring devices (such as, for example, ultra sound) external to the cannula, it would be desirable to have reference markings on the cannula itself so that the medical personnel performing the procedure can have a direct way of perceiving how deeply the cannula is being inserted.

The desired reference mark should be smooth, having minimum porosity so as to lessen the potential for entrapping microorganisms or other contaminants—the cannula being more readily autoclaved and sterilized. It would seem to be the case that markings in the nature of paint on the cannula are relatively undesirable because of relatively high porosity. Such markings would also constitute another foreign substance introduced into the body and would seem to be undesirable for that reason as well.

The desired reference mark should be precisely and economically applied, having a high degree of accuracy in placement and in thickness at a reasonable cost. It would seem to be the case that attempts to create reference marks by etching procedures, including acid etching of a groove into the cannula, are undesirable because they not only introduce a cavity where contaminants might be trapped but also because of the difficulty of precise placement at a reasonable cost.

One way to create a smooth, precise, and economical reference mark on a stainless steel tube is by using a laser. A laser can be so adjusted as to avoid penetrating, or etching a groove into, the metal tube. Instead, the laser can be set so as to discolor the surface of the metal tube by oxidizing a thin layer of the metal. A problem that makes the use of a laser difficult on thin walled metal tubing, such as a cannula, is that lasers naturally generate heat. Excessive localized heating applied to a thin walled metal tube can cause warping and burning of the metal. An unacceptable distortion of the tube interior can result.

Accordingly, it can be seen that there is a need for an apparatus by which high contrast reference marks can be placed on a cannula. Preferably, a laser, in cooperation with a cooling system and an incrementing system, would place smooth and precise marks on a cannula in such a way as to avoid the problems of excessive localized heating to the cannula walls and resultant distortion. Also, a method of using a laser system to place such marks would be required. Of course, the apparatus and method should be economical and should be able to produce precisely marked cannula to various specifications.

SUMMARY OF THE INVENTION

The laser marking apparatus of this invention includes: a laser for marking a thin walled tube; a support system, including a housing, for holding the tube; a cooling system, for injecting a coolant into the tube while it is being marked by the laser; and an incrementing system, for incrementally moving the tube or laser relative to each other. Optionally, there is also provided a rotation system for rotating the tube while it is being marked, in order to provide a circumferential band around the tube, if desired.

The various systems of this invention cooperate so that a tube, held in the housing of the support system, is exposed to the laser, but in a manner specifically designed to minimize excess heat to the thin walls of the tube. Heat minimization is accomplished by (a) running a coolant through the interior of the tube while the laser beam is in contact with the tube, so as to cool the wall of the tube, and (b) dividing a specified mark width into discrete marks, each separated by an unmarked space, and making several incrementally spaced marks so that a series of thin laser marks (rather than a single, wide mark) is placed on the tube to create the perception of a wider mark without generating the heat characteristics of a wider mark.

In a preferred embodiment, the coolant is part of a cooling system and is contained within a recirculating fluid circuit, including a reservoir with hoses attached to the support system to bring coolant into one end of the tube through the housing of the support system, and to return coolant to the reservoir from a drain at the other end of the tube. The temperature and the flow rate of the coolant can be controlled in order to create precise, and reproducible, results.

In a preferred embodiment, there is also an incrementing system that is adjustable to produce a series of thin marks, each separated by a small space so as to create the appearance of a single thicker mark, but without the heat characteristics generated by a thicker mark. It may be desirable, for example, to place a one-millimeter-long high contrast reference mark along a cannula. Rather than scan the laser over a one millimeter section of the cannula to produce a one millimeter-wide mark, the specified width is divided and a series of more narrow marks is produced. For example, an acceptable one millimeter mark can be simulated by producing four marks, each about 0.005" thick, with each mark separated by a small space (for example, a space of about 0.006").

The various systems of this invention are designed so that coolant can be directed into the interior of the cannula, and so that the cannula and laser can be incrementally adjusted relative to one another to produce a series of thin marks. The method of this invention includes the steps of cooling the inside of the cannula, and of resolving a specified mark thickness into a series of relatively more narrow marks separated by unmarked spaces.

It is a specific object of this invention to produce high contrast precision markings on a thin walled metal tube, such as a cannula used in medical procedures. The apparatus and method of this invention employ a laser to solve the problems that have made non-laser marking undesirable. At the same time, the apparatus and method of this invention use the laser in such a way as to minimize the heat-related problems that have heretofore made laser marking unfeasible.

Other objects and uses of this invention will become apparent in the remainder of this disclosure.

DESCRIPTION OF THE DRAWINGS

FIG. 4 is a front elevational view showing certain details of the rotation system of this invention.

FIG. 5 is a side elevational view of a cannula, showing a set of spaced apart marks produced according to the method of this invention.

DETAILED DESCRIPTION OF THE INVENTION

This invention is an apparatus and method for marking thin walled tubes. In a preferred embodiment, this invention uses a laser to mark metal cannula, with the metal typically being stainless steel.

Figure 1:
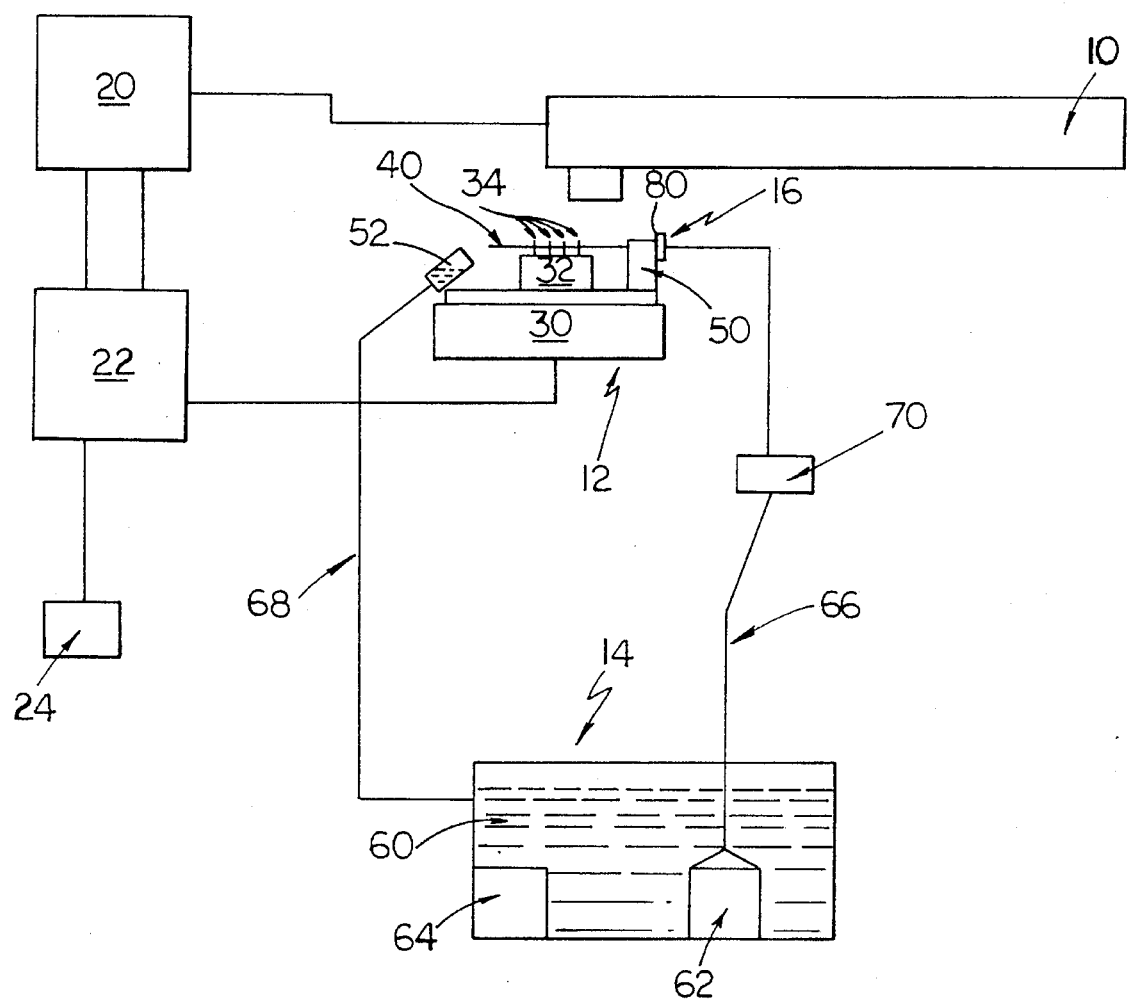
FIG. 1 is a schematic view, showing the various systems of the apparatus of this invention.

With reference to FIG. 1, which is a schematic diagram and not to scale, it can be seen that the apparatus of this invention includes a laser 10; a support system 12, for holding the work piece; a cooling system 14, for cooling the workpiece; an incrementing system (not separately numbered), for incrementally moving the workpiece and the laser relative to one another; and a rotation system 16, for rotating the workpiece.

In the discussion which follows, the various systems of this invention, and the components of each, will be discussed, in overview. Following this, there will be a description of a preferred embodiment and a method of using this invention to mark a thin walled tube.

Overview

Referring to FIG. 1, the laser 10 is a Nd/YAG type, or similar, laser having approximately 50 to 70 watts total carrier wave (CW) output power; an adjustable aperture for producing an adjustable laser beam spot size; and a solid state shutter for operating in a pulsed on/off mode ("Q switched mode"). The laser 10 also is equipped with digital in/out connection (not separately numbered) to a digital computer 20 which is capable of generating "hand shake" signals with an external controller 22. In addition, the laser 10 has mirrors and focusing lenses (not separately numbered), including a galvanometer-controlled mirror for X-axis movement of the laser beam and a galvanometer-controlled mirror for Y-axis movement of the beam.

Lasers and laser computer/controllers such as described above are well known and will not be discussed further herein. Lasers having the characteristics described are readily available in the United States from several commercial suppliers, including JEC, Quantrad, Control Laser, and AB Laser (although it is possible that Control Laser is no longer in the business of selling new laser systems). The applicant has successfully used a JEC "2500" brand 50 watt CW Nd/YAG laser and has also successfully used a Quantrad "Comet" brand 70 watt CW Nd/YAG laser.

The support system 12 includes a linear table 30 (an "X-Y Table"), on which a fixture 32 is mounted. The fixture 32 has a series of support posts 34. The support posts 34 are disposed in-line, and each support post 34 has a groove (not separately numbered) on its top surface. A cannula 40 can be supported by the support posts 34 of the fixture 32, with the grooves of the support posts orienting the cannula in place.

On one side of the fixture 32, of the support system 12 there is an arm 50, and on the other side of the fixture 32 there is a drain 52. As will be explained in more detail later (and as is shown in more detail in FIGS. 2, 3, and 4), the arm 50 contains a seal mounted in a rotating housing through which a coolant can be injected into the cannula 40, with the seal reducing leakage of the coolant and with the rotating housing designed to permit continued injection of coolant while the cannula is rotating. As will be explained in more detail later, the drain 52 collects the coolant as it exits the other end of the cannula. These features will be further explained later, but for now it is sufficient to note them in overview so that the various systems of the invention can be seen schematically and generally.

The cooling system 14 includes a fluid reservoir 60 having a pump 62 to move a coolant through the system, and a thermostat-controlled heater 64 to control the temperature of the coolant. There is a water pipe 66 leading from the fluid reservoir 60 to a stationary delivery tube (not separately numbered or shown in FIG. 1, but shown and discussed later, in connection with FIGS. 2, 3 and 4) that feeds into the arm 50 of the fixture 32 of the support system 12.

As previously summarized, and as will be discussed in detail later, the coolant passes through a housing in the arm 50 and into the interior of the cannula 40. The coolant exits the cannula and passes into the drain 52. To complete the coolant circuit, so as to recirculate coolant within the system, there is a return pipe 68 which leads from the drain 52 back to the reservoir 60. Finally, between the reservoir 60 and the arm 50, there is a metered flow valve 70 by which the flow rate of coolant through the pipe 66 can be adjusted.

The incrementing system (not separately numbered) includes two distinct incrementing devices for moving the cannula 40 and the beam of the laser 10 relative to one another. One incrementing device is mechanical and is associated with the X-Y table 30. The other incrementing device is optical and is associated with the laser 10. Each of the incrementing devices will be discussed, in turn.

The mechanical incrementing device includes the X-Y table 30 which is motor actuated by an electronic controller 22 so as to move the table in one direction only, along the axis of the cannula 40 (the fixture 32 is mounted on the X-Y table so that the axis of the cannula will be disposed appropriately). The controller 22 is operatively connected to the computer 20 which directs the laser 10.

The mechanical incrementing device is initiated by switching the controller "on" by a switch 24. Once turned on, the controller 22 communicates with the computer 20 by digital "hand shake" signals initiating a program so that the controller will: (a) move the table 30 a given distance, (b) send a signal to the computer 20 telling the laser 10 to begin marking, (c) wait for a signal from the computer telling it that the marking is complete, and then (d) repeat steps (a)

through (c) until a given number of marks has been rendered. After the given number of marks has been rendered, the system returns to a ready state, to await the next initiation of the program by a subsequent operation of the switch 24.

The optical incrementing device is included within the laser 10 as previously specified. As previously described, the laser has mirrors and focusing lenses (not separately numbered), including a galvanometer-controlled mirror for X-axis movement of the laser beam and a galvanometer-controlled mirror for Y-axis movement of the beam. With the table 30 stationary, the laser 10 is optically stepped along one of its axes. The laser can be moved along the axis of the cannula 40 by using the galvanometer controlled mirror for the X-axis of the laser. The Y-axis can be disabled to prevent movement of the beam in that direction. The optical incrementing device is actuated by adjustments to the X-axis driver of the laser 10. The X-axis driver is a readily available feature of laser systems, and its use for purposes such as described herein should be readily apparent to one skilled in the art.

The rotation system 16 includes a motor (not visible in FIG. 1, but shown in FIG. 4 and discussed later) which is operatively connected to a pulley 80. As will be discussed in more detail later, the pulley 80 is fixed to a housing in which the cannula 40 is seated so that rotation of the pulley 80 will cause the cannula to rotate.

A Preferred Embodiment

Having provided an overview of the various systems of this invention, including the laser 10, the support system 12, the cooling system 14, the incrementing system, and the rotation system 16, a preferred embodiment will now be described, as will the use of the various systems.

The laser 10 has previously been described (with reference to FIG. 1) as a Nd/YAG type having approximately 50 to 70 watts CW output power; an adjustable aperture for producing an adjustable laser beam spot size; and a Q switched mode. In a preferred embodiment, using a JEC "2500" 50 watt CW laser to place a one millimeter mark on cannula made of 304 stainless steel, having wall thicknesses from 0.006" to 0.009" and having outside diameters of 0.032" and 0.050", the following settings have been found to produce good results.

Laser beam spot size (as set by the adjustable aperture): approximately 0.005"

Laser output power (with the beam spot size at about 0.005"): approximately 8 watts Q switch frequency: in the range of 5,000 to 25,000 cycles per second, and, optimally, between 10,000 to 20,000 cycles per second.

The laser beam spot size was selected in order to create a fine line on the cannula (that is, the line will be approximately 0.005" in width). At this beam spot size, the output power will produce a mark having a darkness sufficiently high to produce an acceptable high contrast mark. The Q switch frequency is set in the indicated range, so as to be high enough to avoid producing a deep groove etched into the cannula (at, for example, a Q switch frequency closer to 1,000 cycles per second, such etching has been encountered). Instead, and within the indicated Q switch frequency range, the metal of the cannula is simply discolored, as the heat of the laser oxidizes a thin layer of the cannula wall.

The result of these laser settings on the cannula is to produce a very fine mark, approximately 0.005" wide, which is relatively dark, and which is relatively shiny and smooth (non-porous). It should be observed that the laser 10 is fixed with reference to the table 30 and the fixture 32 so that the laser beam can play along the axis of the cannula 40. It should also be observed that the foregoing settings are examples only, specific settings can vary in light of the cannula materials and dimensions.

The support system 12 has previously been described (with reference to FIG. 1) as including a linear table 30 (an "X-Y Table"), on which a fixture 32 is mounted. The fixture 32 has a series of support posts 34. On one side of the fixture 32, of the support system 12 there is an arm 50, and on the other side of the fixture 32 there is a drain 52.

Figures 2, 2A:
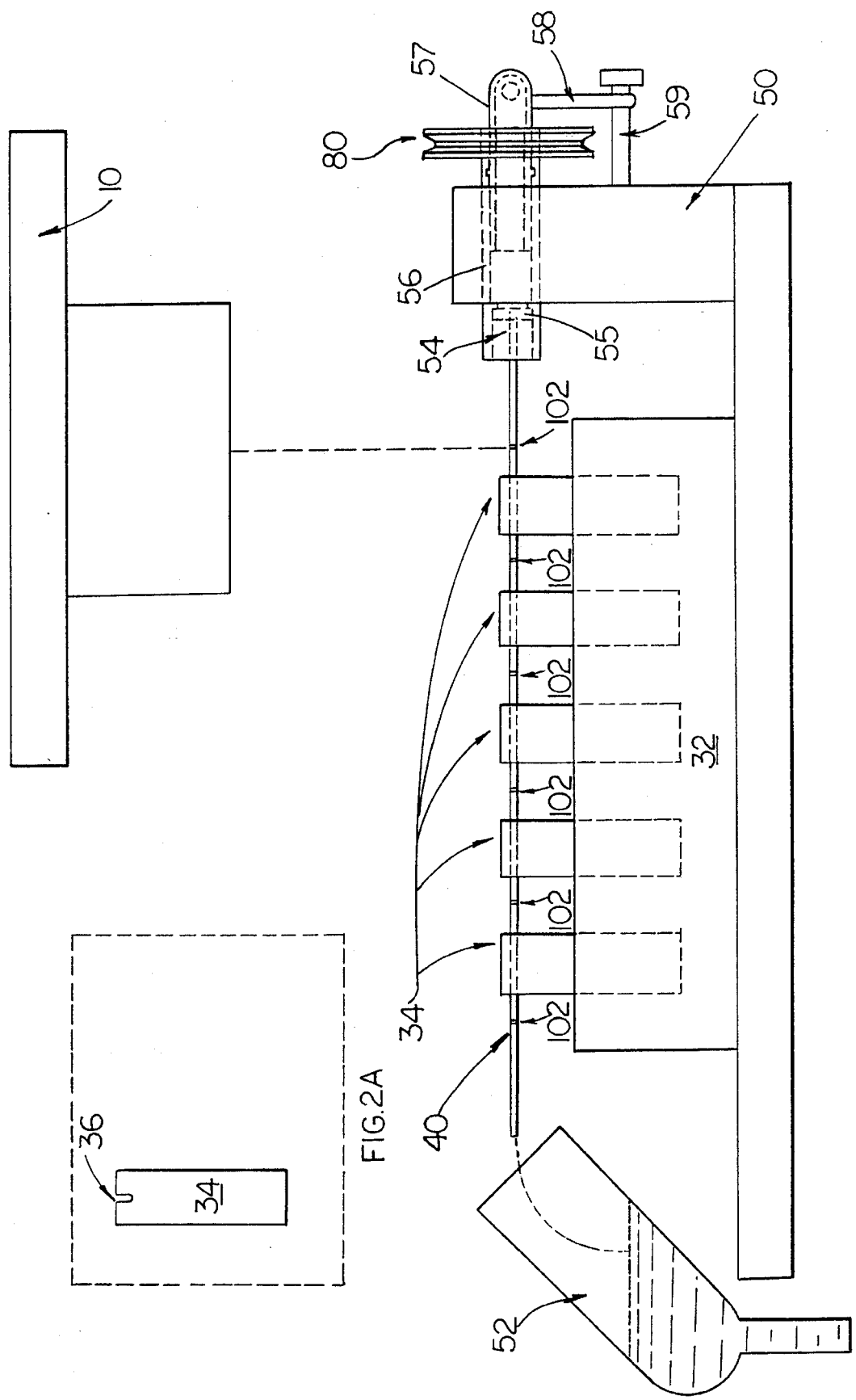
FIG. 2 is a side elevational, partly schematic view showing certain details of the laser marking system, the support system, the rotation system and the cooling system of this invention.
FIG. 2A is a front elevational view of one of the support posts of the support system of this invention.

With reference now to FIG. 2, it can be seen that the cannula 40 is supported on the support posts 34, resting in a groove 36 (better seen with reference to FIG. 2A) on the top surface of each of the support posts.

With reference to FIG. 2, it can also be seen that the arm 50 contains a seal 54 mounted in a rotating housing 56 through which a coolant can be injected into the cannula 40, with the seal reducing leakage of the coolant. The arm also contains a stop ring 55; a rotating housing 56; and a stationary delivery tube 57 having an arresting arm 58. The arm 50 also supports a stop member 59 which is designed to engage the arresting arm 58 of the stationary delivery tube 57 to prevent the delivery tube from rotating. The rotating housing is rotated by action of the pulley 80 (to be discussed later).

Figure 3:
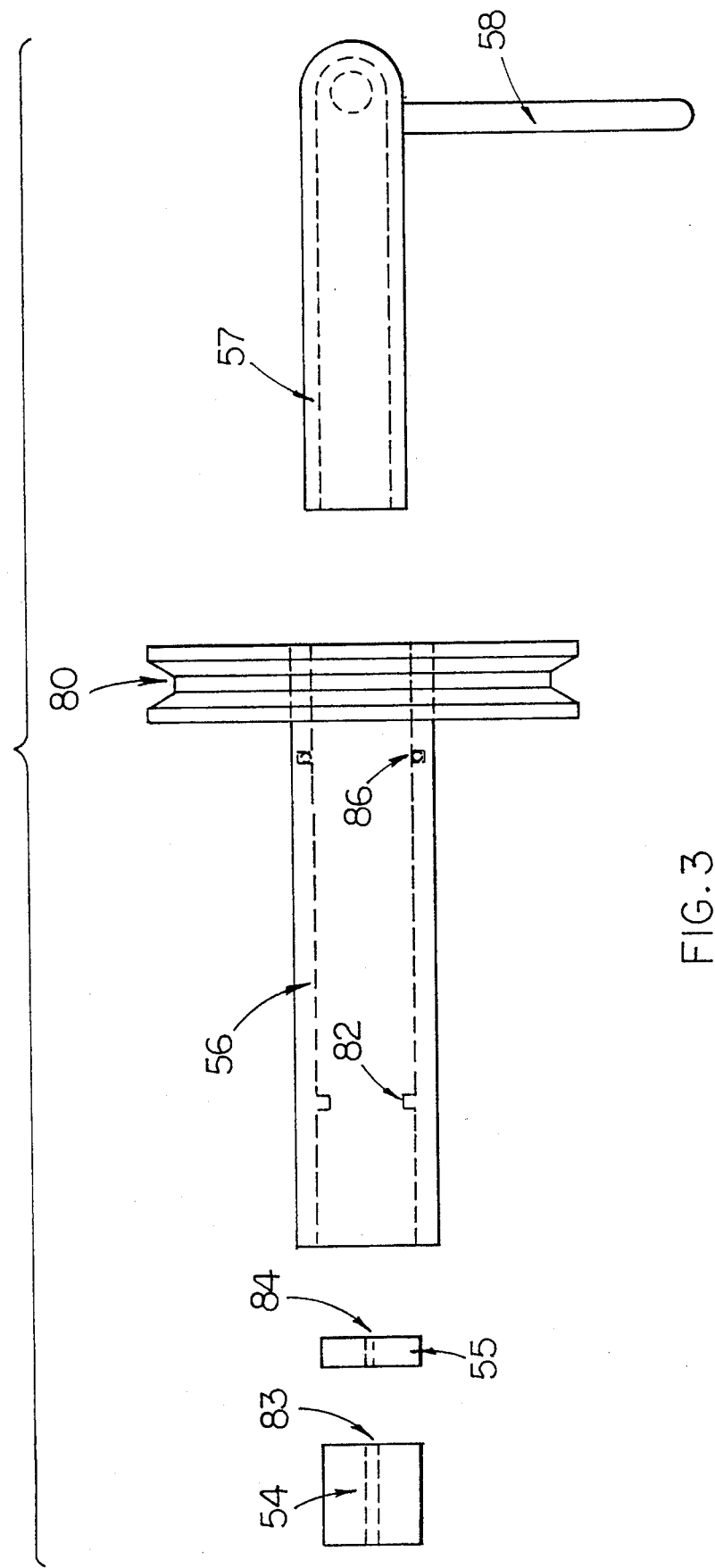
FIG. 3 is a side elevational, exploded view showing certain details of the housing of the support system of this invention.

Certain of the fittings of the rotating housing 56 can be better understood with reference to FIG. 3. Near one end of the rotating housing 56, is an annular groove 82 upraised from the interior wall of the housing. The stop 55 is friction-fitted and seated against the upraised groove 82. The seal 54, is friction-fitted and seated against the stop 55. The seal 54 has a center hole 83; the stop has a center hole 84.

Near the other end of the rotating housing 56 is an annular groove 86 which is recessed into the interior wall of the housing. An O-ring (not shown) can be fitted into the recessed groove 86 to form an inlet seal, sealing the stationary delivery tube 57.

It can now be understood that, in a preferred embodiment of this invention, the cannula 40 (reference FIG. 2) is placed on the fixture 32 as follows: with the cannula 40 resting in the grooves 36 of the support posts 34, the point of the cannula is inserted into the rubber seal 54 of the rotating housing 56 and pushed through the hole 83 thereof until the cannula point comes to rest in the stop ring 55 of the rotating housing 56. The hole 84 of the stop ring is drilled smaller than the inside diameter of the cannula 40 to better effect coolant flow into the cannula. The materials and dimensions of the seal 54 and the stop ring 55 are set so that they provide a friction tight attachment to the cannula 40. The applicant has successfully used a polyurethane rubber for the seal 54 and a DELRIN plastic for the stop ring 55, with the different materials providing for a good seating of the tip of the cannula 40 into the stop ring.

The cooling system 14 has previously been described (with reference to FIG. 1), and the water pipe 66 has been shown to connect the reservoir 60 to the stationary delivery tube 57 (reference FIGS. 2 and 3). Thus, coolant is passed through the stationary delivery tube 57, through the rotating housing 56, and into the cannula 40. As previously discussed, the coolant exits the cannula into the drain 52 and passes back to the reservoir 60 through the return pipe 68. There is a thermostat-controlled heater 64, a pump 62, and a metered flow valve 70. In a preferred embodiment, the pump 62 is a submersible, centrifical pump. Although gravity, ordinary water pressure from a tap, or a reciprocating pump could be used, the centrifical pump has been found to provide a steady, non-pulsating pressure flow.

In a preferred embodiment, using a JEC "2500" 50 watt CW laser to place a one millimeter mark on cannula made of 304 stainless steel, having wall thicknesses from 0.006" to 0.009" and having outside diameters of 0.032" and 0.050", the following settings have been found to produce good results.

Coolant: various coolants may be used, and water has been found to produce good results, Coolant flow rate: in the range of 0.5 to 15.0 cc/minute, optimally, 5.0 to 10.0 cc/minute, Coolant temperature: in the range of 32 to 170 degrees F., optimally, 80 to 90 degrees F.

The combination of coolant, flow rate and temperatures have been found to cool the cannula sufficiently to produce acceptable results without distortion to the cannula and without undue burning of the outside wall. It should be observed that the foregoing settings are examples only, specific combinations can vary, and other coolants can be used.

The incrementing system has previously been described (with general reference to FIG. 1) as including two distinct incrementing devices for moving the cannula 40 and the beam of the laser 10 relative to one another. One incrementing device is mechanical and is associated with the X-Y table 30. The other incrementing device is optical and is associated with the laser 10.

The mechanical incrementing device tends to have the advantage of accuracy, as it is limited only by the tolerances of the X-Y table 30. The optical incrementing device tends to have the advantage of speed, as it does not require mechanical motion. It is possible to practice this invention with (a) a mechanical incrementing device only, (b) an optical incrementing device only, or (c) both devices in combination.

In a preferred embodiment, using a JEC "2500" 50 watt CW laser to place a one millimeter mark on cannula made of 304 stainless steel, having wall thicknesses from 0.006" to 0.009" and having outside diameters of 0.032" and 0.050", both incrementing devices are present, and either one can be used. The following settings have been found to produce good results.

Within a one millimeter thickness, four separate marks are made, with unmarked sections between them, The separate marks are each about 0.005" thick, The space between marks is about 0.006" thick.

To produce such marks and spacing, the laser is moved relative to the cannula after each mark is made. Such movement can be effected by either the mechanical incrementing device or by the optical incrementing device. FIG. 5 shows a cannula having four marks 100 within a one millimeter area so as to create the appearance of a single one-millimeter thick contrast marking 102.

As a further refinement, and also in a preferred embodiment, it can be seen with reference to FIG. 2 that the systems of this invention can be used to produce a number of apparent one millimeter thick marks 102 (each of which is actually four narrow bands separated by a space as shown in FIG. 5). In this example, the invention is used to produce six apparent one millimeter thick marks 102 at intervals of every two centimeters along the length of the cannula 40. The use of such interval marking is to provide a depth gauge so that medical personnel can tell how deeply the cannula is inserted into a body.

In a preferred embodiment of this invention, the two incrementing devices are used cooperatively, and in alternating fashion, to produce this result. The cannula is placed in position and the optical incrementing device is used to step the laser at 0.006" intervals to place the four marks which comprise one apparent one-millimeter thick mark 102. The mechanical incrementing device is then used to move the table 30 two centimeters so as to expose another segment of the cannula to the laser beam; and the optical incrementing device is then used to place another set of four marks within a one-millimeter range starting at this point. This procedure is repeated so as to form the desired number of marks at the desired intervals along the cannula.

As previously discussed, the controller 22 and computer 20 can be made to perform this sequence of actions using a program of the type previously discussed. It should be observed that the foregoing settings are examples only, specific settings can vary in light of the desired specifications.

The rotation system 16 has previously been described (with general reference to FIG. 1) as including a motor (not visible in FIG. 1) which is operatively connected to a pulley 80. With reference now to FIG. 3, it can be seen that the pulley 80 is fixed to the rotating housing 56 in which the cannula 40 is seated (reference FIG. 2) so that rotation of the pulley will cause the cannula to rotate.

The rotation system can be better understood with reference to FIG. 4. It can be seen that the motor 90 is attached to the fixture 32, and that the motor has a motor pulley to which a drive belt 94 is attached. The drive belt 94 is also attached to the pulley 80 previously described. This pulley 80 is the pulley that is connected to the rotating housing 56 that is contained within the arm 50 of the support fixture 32.

FIG. 4 also serves to illustrate the working of the arresting arm 58 of the stationary delivery tube 57. As the arresting arm 58 is engaged against the stop member 59 (assuming that the pulley 80 is being driven in a counterclockwise direction), any tendency of the stationary delivery tube 57 to rotate is checked. As a result, the stationary delivery tube 57 will remain relatively motionless as the rotating housing 56 revolves around it.

The rotation system allows the cannula to be rotated beneath the laser beam. This will produce a mark around the circumference of the cannula.

Method of Producing Marks on Thin Walled Tubes

From the foregoing discussion, the method of this invention should now be apparent. Because laser light by nature generates heat, a method is required to control localized heating of thin wall tubing which is to be marked by a laser.

The method of this invention, using the apparatus and systems previously described, includes the prevention of excessive localized heating by passing a coolant through the tubing while the laser light is in contact with the surface of the tube. A coolant seal 54, as previously described, is employed to ensure that the coolant is channeled through the interior of the tubing while preventing leakage of the coolant onto the surrounding area or exterior surface of the tubing.

If the marks are to be circumscribed around the tubing, a method of rotating the tubing while maintaining the integrity of the coolant seal 54, as previously described, is employed. If several marks are to be placed at intervals along the tube, a method of incrementally moving the cannula relative to the laser beam, as previously described, is employed.

The method of this invention, using the apparatus and systems previously described, also includes the prevention of excessive localized heating by dividing a specified mark thickness into a series of relatively more narrow marks, each separated by an unmarked area. It has been found, for example, that while scanning the laser beam over a one-millimeter area to produce a single, solid one-millimeter mark produces unacceptable results, the method of this invention (including, for example, placing four marks of about 0.005" each within a one-millimeter wide area) produces an acceptable high contrast mark without undue heating and distortion to the thin walled tube.

It has been found, in general, that two steps of this invention are particularly effective in allowing the marking of thin wall stainless steel tubing with a laser without distortion of the tubing. Those steps involve: (a) using a coolant, and (b) breaking a desired mark thickness into a series of more narrow marks, each of the more narrow marks separated by an unmarked space.

Finally, the product produced according to the method of this invention is a marked thin walled metal tube, as previously described, and having the characteristics previously described.

From the foregoing description, the apparatus and method of this invention should be apparent, as is the product produced thereby. The specific examples given are by way of illustration only, and not by way of limitation.

What is claimed is:

1. A method for marking a stainless steel tube having an interior cavity and an exterior wall, comprising the steps of:
   (a) injecting a coolant into the interior cavity of said tube; and
   (b) irradiating an Nd/YAG laser beam to the exterior wall of the tube thereby producing at least one mark thereon, said tube having an exterior wall thickness in the range of 0.006 inches to 0.009 inches and having an outside diameter in the range of 0.032 inches to 0.050 inches, wherein said step of irradiating an Nd/YAG laser beam to the exterior wall of the tube further comprises heating the exterior wall of the tube sufficiently to cause oxidation thereon while said coolant cools the interior of the tube sufficiently to prevent damage to the tube as heat is applied; said oxidation creating a first dark oxide mark on the exterior wall of the tube.

2. The method of claim 1, wherein said tube has a longitudinal axis and the step of irradiating an Nd/YAG laser beam to the exterior wall of the tube further includes the step of rotating said tube about its axis while maintaining at least a portion of said coolant within the tube while irradiating said laser beam to the exterior wall.

3. The method of claim 1, wherein said step of irradiating an Nd/YAG laser beam to the exterior wall of the tube further includes the step of continuing to inject coolant into the interior cavity of the tube while irradiating said laser beam to the exterior wall.

4. The method of claim 1, wherein said tube has a longitudinal axis and the step of irradiating an Nd/YAG laser beam to the exterior wall of the tube further includes the steps of:
   (a) rotating said tube about its axis while maintaining at least a portion of said coolant within the tube; and
   (b) continuing to inject coolant into the interior cavity of the tube as the tube is being rotated while irradiating said laser beam to the exterior wall.

5. The method of claim 1, further comprising the steps, after the step of irradiating an Nd/YAG laser beam to the exterior wall of the tube, of:
   (a) moving said tube and said laser relative to one another after creating said first dark oxide mark;
   (b) again irradiating said laser beam to the exterior wall of the tube, thereby heating the exterior wall of the tube sufficiently to cause oxidation thereon; said oxidation creating a second dark oxide mark on the exterior wall of the tube while maintaining at least a portion of said coolant within the interior cavity of the tube, thereby cooling the interior of the tube sufficiently to prevent damage to the tube as the heat is applied.

6. The method of claim 5, wherein said step of moving said tube and said laser relative to one another comprises the step of moving at least one of them longitudinally along an axis parallel to the axis of the tube.

7. The method of claim 6, wherein said first and second oxide marks have a width, and the step of moving said tube and said laser relative to one another is by a distance which is less than or equal to the width of one of said first and second oxide marks.

8. The method of claim 6, wherein said step of moving said tube relative to said laser is by a distance which is greater than the width of one of said first and second oxide marks.

9. The method of claim 6 wherein said step of moving said tube and said laser relative to one another is such that the two marks are within one millimeter of one another.

10. The method of claim 1 wherein:
   (a) said first dark oxide mark on the exterior wall of the tube has a width of approximately 0.005 inches; and
   (b) said coolant is injected at an adjustable coolant flow rate, said flow rate being set in the range of 0.5 to 15.0 cc/minute; and said coolant is water having a temperature in the range of 32 to 170 degrees F.

* * * * *